United States Patent
Wu et al.

(10) Patent No.: US 10,525,008 B2
(45) Date of Patent: Jan. 7, 2020

(54) MICROENCAPSULATED AMINO ACID COMPOSITION AND THE METHOD OF MANUFACTURING THE MICROENCAPSULATED AMINO ACID COMPOSITION

(71) Applicant: INNOBIO Corporation Limited, Dalian, Liaoning (CN)

(72) Inventors: Wenzhong Wu, Dalian (CN); Jianbin Chen, Dalian (CN); Yuemei Zhang, Dalian (CN)

(73) Assignee: INNOBIO CORPORATION LIMITED, Dalian, Liaoning (CN)

(*) Notice: Subject to any disclaimer, the term of this patent is extended or adjusted under 35 U.S.C. 154(b) by 995 days.

(21) Appl. No.: 14/052,312

(22) Filed: Oct. 11, 2013

(65) Prior Publication Data

US 2014/0105994 A1  Apr. 17, 2014

(30) Foreign Application Priority Data

Oct. 12, 2012  (CN) .......................... 2012 1 0386959

(51) Int. Cl.
*A61K 9/16* (2006.01)

(52) U.S. Cl.
CPC .......... *A61K 9/1605* (2013.01); *A61K 9/1652* (2013.01); *A61K 9/1682* (2013.01)

(58) Field of Classification Search
CPC ... A61K 9/1605; A61K 9/1652; A61K 9/1682
USPC ....................................................... 424/494
See application file for complete search history.

(56) References Cited

U.S. PATENT DOCUMENTS

2010/0158984 A1*  6/2010  Qvyjt ................... A61K 9/0095
                                                             424/439

FOREIGN PATENT DOCUMENTS

| CN | 101658244 A | 3/2010 |
|---|---|---|
| CN | 101744110 A | 6/2010 |
| CN | 101744111 A | 6/2010 |
| EP | 0237506 A1 | 9/1987 |
| EP | 0622083 A1 | 11/1994 |
| EP | 1475089 A1 | 11/2004 |
| EP | 2324826 A1 | 5/2011 |
| FR | 2795962 A1 | 1/2001 |
| JP | 2003155232 A | 5/2003 |
| WO | 2013109863 A1 | 7/2013 |

* cited by examiner

*Primary Examiner* — Adam C Milligan
(74) *Attorney, Agent, or Firm* — Novick, Kim & Lee, PLLC; Allen Xue

(57) ABSTRACT

The invention relates to a microencapsulated amino acid composition and methods of manufacturing this composition. Amino acids, such as branched-chain amino acids, have low water solubility, poor hydrophilicity, and poor stability. Amino acids are thus difficult to be digested and absorbed. Consequently amino acids can hardly meet human needs of consuming. This microencapsulated amino acid composition that can quickly disperse and dissolve in cold water, resulting clear solution. The method includes (1) adding coating agents, wetting agents, or other excipients to the amino acid mixture, (2) modifying the surface of microencapsulated particles to considerably accelerate the wetting speed. In this composition, the weight ratio of amino acids and excipients is from 100/0.1 to 100/10.0.

7 Claims, No Drawings

MICROENCAPSULATED AMINO ACID COMPOSITION AND THE METHOD OF MANUFACTURING THE MICROENCAPSULATED AMINO ACID COMPOSITION

FIELD OF TECHNOLOGY

The invention relates to a microencapsulated amino acids composition and methods of manufacturing this composition. Amino acids, such as branched-chain amino acids, have low water solubility, poor hydrophilicity, and poor stability. This invention delivers advantages over conventional products, such as instant dispersion and dissolution in water, transparent and stable solution. The microencapsulated amino acids composition in the present invention does not change color before the expiration date of the composition, and does not have unpleasant taste or odor that prior amino acids bring to consumers.

BACKGROUND KNOWLEDGE

Amino acid is a generic term for a class of organic compounds containing amino and carboxyl group. Amino acids are basic composing units of protein, which ensures normal physiological activities of human bodies. For example, the Branched Chain Amino acids (BCAA), including l-leucine, l-isoleucine, and l-valine, are essential to human bodies. The composition of BCAA can reduce fatigue, coordinate endocrine, improve immunity, prolong life, and other effects.

The composition of BCAA can prevent muscle from decomposing or losing nutrient. It can increase muscle capability of resisting pressure. It can also promote the synthesis of protein metabolism after exercises, speed up the synthesis of muscle, reduce muscle tissue decomposition, and help to increase muscle mass without any side effects. They are the indispensable nutritional supplements for bodybuilders and athletes.

Currently, amino acids products in markets are in the form of tablets, capsules, or powders. Among them, tablets and capsules give consumers a feeling of medicines. And consumers have to consume 5-20 g daily doses to reach desired results. This means consumers must take a number of tablets or capsules, which is a burden to consumers. Powder products cannot dissolve quickly into water, and will float on the surface of water. It generally takes 20 min to slowly dissolve 2 g amino acids into 100 ml 25° C. water. This is also inconvenient for consumers.

Among The existing technologies, lipophilic excipients, for example, fatty acids, wax, beeswax, are often used as coating materials. China Patent Application (Publication No. CN101744110A) provides an amino acids microencapsulating method. This method involves using high freezing point stearic fatty acid ester as coating material. The coating material is melted and mixed with the active amino acid, to obtain coated microencapsulated particles. This method only resolved the problem of embedding amino acids; the product, however, cannot quickly dissolve in water. And the product has low bioavailability and limited application.

China Patent Application (Publication No. CN101658244) discloses a microencapsulated amino acids product used lipophilic material as coating material. The product has sustained release and controlled release capability. But this method does not answer the market demand of a highly dispersible, quickly dissolvable amino acids product.

China Patent Application (Publication No. CN1658862A) discloses a method of manufacturing BCAA particles. That invention introduced organic acid into mixture of amino acids to increase volume ratio and to reduce dosage volume. That invention, however, still used capsules or tablets as dosage form of the active ingredient. Compared with the instant dissolvable particle products, that invention is still difficult to take for consumers, especially for consumers who have difficult in swallowing. The bioavailability of that invention is low. The evaluation of the invention's stability has not been found.

CONTENT OF THE INVENTION

The purpose of the present invention is to provide a microencapsulated amino acids composition that can quickly disperse and dissolve in cold water, resulting clear solution. To achieve this purpose, the microencapsulated amino acid composition is prepared by adding raw material mixture that containing amino acids into water or aqueous ethanol solution, then granulating and drying the composition; the composition composes the following components:
(a) One or more amino acids mixed in any proportion;
(b) Excipients: includes coating agents and wetting agents.

This invention also provides a microencapsulated amino acids composition that is prepared by adding raw material mixture that containing amino acids into water or aqueous ethanol solution, then granulating and drying the composition. The composition composes the following components:
(a) One or more amino acids mixture in any proportion;
(b) Excipients: includes coating agents or wetting agents.

In the present invention, the coating agents used for the microencapsulated amino acids composition is composed of one or a mixture of any the following: starch, vegetable gums (such as: gum arabic, carrageenan, etc.), proteins, dextrin, gelatin, methylcellulose, sodium carboxymethyl starch, sodium carboxy methyl cellulose, low-substituted hydroxypropyl cellulose, hydroxypropyl methyl cellulose, polyvinyl pyrrolidone, acrylic polymers, and polyethylene glycolin. That is, the coating agents used for the microencapsulated amino acids composition is composed of at least one of the following: gum arabic, sodium carboxy methyl starch, hydroxypropyl methyl cellulose, sodium carboxy methyl cellulose, methyl cellulose. Preferably of one or a mixture of any proportion of any of the following: gum arabic, carboxy methyl cellulose sodium, carboxy methyl starch sodium, and hydroxypropyl methyl cellulosein. Most preferably of one, or a mixture of any two in any proportion, or a mixture of any three in any proportion of the following: gum arabic, carboxy methyl starch sodium, and hydroxypropyl methyl cellulosein. The Arabic gum is a natural gum acacia purified extract, and its derivatives.

In the present invention, the wetting agents used for the microencapsulated amino acids composition is composed of one or a mixture of the following: phospholipids, sucrose fatty acid esters, sorbic alcohol fatty acid esters, polyglycerol fatty acid esters, sodium stearoyl lactylate, gum arabic, and modified starch. Preferably of one or a mixture of any proportion of any the following: phospholipids, sodium stearoyl lactylate, sucrose fatty acid esters, and polyglycerol fatty acid ester. More preferably of one, or a mixture of two in any proportion, or a mixture of any three in any proportion of the following: phospholipids, sucrose fatty acid esters, and polyglycerol fatty acid ester.

The phospholipids are extracted from vegetable oils, including concentrated phospholipids, phospholipids powder (de-oiled phospholipids), lecithin, and structurally modified phospholipids. "Modified" refers to the modification of the industry-known methods and processes, including acetylation, hydroxylation, sulfonation, hydrogenation, and enzymatic modification, etc.

The sucrose fatty acid ester, i.e. sucrose esters of fatty acids or sucrose esters, referred to as SE (SUGAR ESTERS) is a simple substance or a mixture from sucrose and fatty acids by esterification reaction. Including sucrose stearate, sucrose oleate, sucrose palmitate, sucrose laurate, the hydrophilic lipophilic balance value (HLB value) is 6-16 preferably.

The polyglycerol fatty acid esters, also known as polyesters, include polymerization degree from trimer to decamer fatty acid esters of oleic acid, stearic acid, and lauric acid. Its hydrophilic-lipophilic balance value (HLB value) is 8 to 18 preferably.

In the present invention, the microencapsulated amino acids composition component (a) of raw materials mixture is leucine, isoleucine and valine in one or a mixture of any two or any three in any proportion. Wherein the single amino acid is preferably to use leucine; mixed amino acids are preferably to use leucine, isoleucine, or valine at a mass ratio of 1.5 to 8.5:1:1 to 2; preferably at the ratio of 1.5~4.5:1:1~2.

In the present invention, the preferred technical solution for the microencapsulated amino acid composition has the mass ratio of components (a) and (b) of raw material mixture 100:0.1 to 10.0, preferably 100:0.3 to 5.0.

In the present invention, the microencapsulated amino acid composition can disperse in water within less than 20 seconds and can dissolve in water into transparent within less than 10 minutes, turbidity is less than 30 NTU.

In this invention, "water dispersion" refers to the water dispersion rate of the combined amino acid particles and the "precipitation" rate of the particles as well. "Water dispersion" is determined by the following experimental method. 100 ml of 25 pure water is added to a 150 ml beaker and placed still for 15-45 s till there are no air bubbles in the water and surface of water is smooth. 2 g of the amino acid particles (accurate to 0.01 g) are quickly poured into the prepared water 50 mm over the beaker. The time of all samples get wet and "precipitate" onto the bottom of the beaker is recorded as T1, s, which is the time of "water dispersion".

In this invention, "water-dissolved clearness time" represents the time of the combined amino acid particles dissolve completely in water by stirring or vortexing till the solution becomes cleared by naked eyes. "Water-dissolved clearness time" is determined by the following experimental method. 2 g of the amino acid particles (accurate to 0.01 g) are added to a 150 ml beaker, which contains 100 ml of 25 pure water. The solution is stirred with a steady speed of 140-160 r/min till the amino acid particles dissolve completely in water. The completely dissolved solution is characterized as clear without precipitants or floating particles. The time of the complete dissolving process is recorded as T2, min.

In this invention, "water solution turbidity" is applied to describe the clearness of the combined amino acid solution and determined by the following experimental method. 2 g of the amino acid particles (accurate to 0.01 g) are added to a 150 ml beaker, which contains 100 ml of 25 pure water. The solution is stirred with a steady speed of 140-160 r/min till the amino acid particles dissolve completely in water. The completely dissolved solution is characterized as clear without precipitants or floating particles. The turbidity of the amino acid solution is measured by the turbidimeter and recorded.

The other purpose of this invention is to provide the preparation method of the microencapsulated combined amino acids described above. The preparation method includes the following steps:

A. mix the component (b) from raw materials with water or ethanol solution to make the I mixture;

B. add the mixture I from step A to the a component to get the II mixture;

C. put the mixture II from step B into the granulator to prepare combined particles by particle grouping;

D. air dry the combined particles from step C.

In this invention, the microencapsulated combined amino acids are covered by microfilms through the addition of wetting agents to the particle surface. At the same time, the exterior modification by excipients materials greatly increases the water dampening rate of the combined particles, makes the quick dispersion of the particles in water, and achieves the instantized dissolution effects of the combined particles. The microencapsulated combined amino acids in this invention have greatly increased the water dispersion rate compared to other combined amino acid products with current technology, which is demonstrated through experiments. At the same time, the amino acids solution is clear without precipitants, or floating particles, or any foaming. The microencapsulated combined amino acids have a stable shelf life, easiness for handling and application, and a high bioavailability.

Amino acids products have a special taste, which makes it difficult for elderly and children to intake these products orally. A huge amount of sweetener has been used to cover the special taste of amino acids in current technology for an easy ingestion. However, the use of sweetener brings another potential dangerous factor for human health. The wetting agents or coating agents used in this invention microencapsulate amino acid particles and competently conceal their special taste. When the invented composition dissolves in water, the coating agents or wetting agents still cover the surfaces of amino acid molecules to reduce the special taste for oral intake of the amino acids. On the other hand, the coating agents or wetting agents conceal the taste of amino acids, which makes the invented product reach the quality standards for the taste of amino acid products and has never been achieved by currently available technology.

The beneficial effects of this invention:

1. The instantized amino acids composition particles produced by this invention have a better water dispersion and instantiation feature. Therefore they are easier and more convenient to handle and ingest, and easy for human body to quickly absorb.

2. The instantized amino acids composition solution is clear without precipitants, or floating particles, or any foaming. The solution has a better visual effect during application and provides a fresh feeling for the consumers.

3. This invented product has a good stability. The senses (smell and taste), color, and instantized solubility of this product fulfill the quality request of products in this area, which has been examined by fastened stability test.

4. The instantized amino acid particles in this invention are prepared through a simple method and processing flow, which makes them easier for industrial scale production.

The invention will now be described in further detail with reference to the following. If there's no extra explanation, all the excipients material used in examples were list in Table 1.

TABLE 1

| Ingredients | A1 | A2 | A3 | A4 | A5 | A6 |
|---|---|---|---|---|---|---|
| Concentrated phospholipids | / | / | 1.75 kg | / | / | / |
| Sucrose fatty acid ester | 0.35 kg | 0.44 kg | / | 0.96 kg | / | 0.75 kg |
| De-oiled phospholipids | / | 2.1 kg | / | / | / | 0.16 kg |
| hydroxypropyl methylcellulose | 0.15 kg | / | 0.71 kg | / | 0.5 kg | / |
| sodium carboxymethy starch | / | / | 0.2 kg | 1.9 kg | 1.72 kg | 0.8 kg |
| Gum arabic | / | / | / | 1.1 kg | / | / |

TABLE 2

| Ingredients | A1 | A2 | A3 | A4 | A5 | A6 | A7 | A8 |
|---|---|---|---|---|---|---|---|---|
| Concentrated phospholipids | / | / | 1.75 kg | / | / | / | / | / |
| Sucrose fatty acid ester | 0.35 kg | 0.44 kg | / | 0.96 kg | 0.85 kg | 0.75 kg | 0.44 kg | / |
| De-oiled phospholipids | / | 2.1 kg | / | / | 0.15 kg | 0.16 kg | 2.1 kg | / |
| hydroxypropyl methylcellulose | 0.15 kg | / | 0.71 kg | / | 0.5 kg | / | / | 0.5 kg |
| sodium carboxymethyl starch | / | 7.5 kg | 0.2 kg | 1.9 kg | / | 0.8 kg | / | 1.72 kg |
| Gum arabic | / | / | / | 1.1 kg | / | / | / | / |

EXAMPLE 1

98 kg BCAAs (Leu:Ile:Val(m:m:m)=2:1:1) mixed with 20.5 kg 75% Ethanol contained A1, then pelleted in high shear granulator and dried 3 h at 80° C. The bulk density of the dry products after griddling was 0.56 g/mL. Two gram final products, putting into 100 mL water at 25° C., dispersed itself within 11 s and dissolved totally in 4 min 30 s. The IBCAAs solution with 12 NTU turbidity appeared clear, no precipitation, no floating and no foaming feature.

EXAMPLE 2

98 kg BCAAs (Leu:Ile:Val(m:m:m)=3:1:1) mixed with 100.5 kg purified water contained A2 then pelleted in suppression & extruding machine and dried. The dry products griddled 35 mesh sieve and the bulk density was 0.62 g/mL. Two gram final products, putting into 100 mL water at 25° C., dispersed itself within 14 s and dissolved totally in 5 min 20 s. The IBCAAs solution with 23 NTU turbidity appeared clear, no precipitation, no floating and no foaming feature.

EXAMPLE 3

98 kg BCAAs (Leu:Ile:Val(m:m:m)=3:1:2) mixed with 15 kg purified water contained A3 then stirred in stirred tank. After fully mixing and shearing 20 min, the homogenized products spray-dried and griddled 35 mesh sieve. The bulk density of the products was 0.35 g/mL. Two gram final products, putting into 100 mL water at 25° C., dispersed itself within 15 s and dissolved totally in 6 min 10 s. The IBCAAs solution with 17 NTU turbidity appeared clear, no precipitation, no floating and little foaming.

EXAMPLE 4

98 kg Leucine mixed with 100 kg purified water contained A4 then stirred in stirred tank. After fully mixing and shearing 20 min, the homogenized products spray-dried and griddled 35 mesh sieve. The bulk density of the products was 0.35 g/mL. 1.5 gram final products, putting into 100 mL water at 25° C., dispersed itself within 8 s and dissolved totally in 4 min 50 s. The Leucine solution with 21 NTU turbidity appeared clear, no precipitation, no floating and little foaming.

EXAMPLE 5

108 kg BCAAs (Leu:Ile:Val(m:m:m)=4:1:1) mixed with 21.5 kg purified water contained A5, then pelleted in Screw extrusion type pelletizer and dried 3 h at 80° C. The bulk density of the dry products after griddling was 0.66 g/mL. Two gram final products, putting into 100 mL water at 25° C., dispersed itself within 16 s and dissolved totally in 8 min 5 s. The IBCAAs solution with 11 NTU turbidity appeared clear, no precipitation, no floating and no foaming feature.

In accelerated test, the packed products tested in 45° C., 75% humidity environment for 3 months and no product quality index changed, including color, odour, taste, dispersibility, instant disperse and turbidity.

EXAMPLE 6

112 kg BCAAs (Leu:Ile:Val(m:m:m)=8:1:1) mixed with 25 kg purified water contained A6, then pelleted in Screw extrusion type pelletizer and dried 3 h at 80° C. The bulk density of the dry products after griddling was 0.66 g/mL. Two gram final products, putting into 100 mL water at 25° C., dispersed itself within 13 s and dissolved totally in 4 min 10 s. The IBCAAs solution with 14 NTU turbidity appeared clear, no precipitation, no floating and no foaming feature.

EXAMPLE 7

110 kg Isoleucine mixed with 68 kg purified water contained A6 then pelleted in suppression & extruding machine and dried. The dry products griddled 35 mesh sieve and the bulk density was 0.62 g/mL. Two gram final products, putting into 100 mL water at 25° C., dispersed itself within 10 s and dissolved totally in 5 min 40 s. The final solution with 23 NTU turbidity appeared clear, no precipitation, no floating and no foaming feature.

EXAMPLE 8

92 kg BCAAs (Leu:Ile:Val(m:m:m)=3:1:1) mixed with 12 kg purified water contained A7 then pelleted in suppression & extruding machine and dried. The dry products griddled 20 mesh sieve and the bulk density was 0.65 g/mL. Two gram final products, putting into 100 mL water at 25° C., dispersed itself within 11 s and dissolved totally in 4 min 20 s. The IBCAAs solution with 17 NTU turbidity appeared clear, no precipitation, no floating and no foaming feature.

EXAMPLE 9

178 kg BCAAs (Leu:Ile:Val(m:m:m)=4:1:1) mixed with 45.2 kg purified water contained A8, then pelleted in Screw extrusion type pelletizer and dried 3 h at 80° C. The bulk density of the dry products after griddling was 0.67 g/mL. Two gram final products, putting into 100 mL water at 25° C., dispersed itself within 14 s and dissolved totally in 7 min 15 s. The IBCAAs solution with 13.6 NTU turbidity appeared clear, no precipitation, no floating and no foaming feature.

In accelerated test, the packed products tested in 45° C., 75% humidity environment for 3 months and no product quality index changed, including color, odour, taste, dispersibility, instant disperse and turbidity.

The amino acids composition produced by this invention showed more instant disperse ability than others. Therefore, it's more convenient for using and more bioavailability for taking, which can be applied in powdered beverages and so on.

What we claim:

1. Granules of amino acid composition, consisting of a homogenous mixture of:
   (a) one or more amino acids that consists of leucine, isoleucine, valine, or mixtures thereof;
   (b) one or more coating agents and one or more wetting agents; and
   (c) water,
      wherein the granules of amino acid composition are obtained by spray-drying or extruding followed by drying and griddling the homogenous mixture so that the component (a) and the component (b) are mixed and homogenously distributed throughout the granules, including the entire surface thereof,
      wherein the one or more coating agents are chosen from gum Arabic, sodium carboxy methyl starch, hydroxypropyl methylcellulose, or mixtures thereof,
      wherein the one or more wetting agents are chosen from phospholipids, sucrose fatty acid ester, or mixtures thereof, and
      wherein the granules, upon oral administration, are perceived to taste significantly better than the raw amino acids.

2. The granules of amino acid composition of claim 1, wherein the weight ratio of the component (a) to the component (b) ranges from 100/0.1 to 100/10.

3. The granules of amino acid composition of claim 1, wherein the composition has a water dispersion of less than 20 seconds.

4. A method of manufacturing the granules of amino acid composition of claim 1, comprising:
   A. mixing water or ethanol with the component (b) to get mixture I;
   B. mixing the mixture I with the component (a) to get mixture II;
   C. granulating the mixture II in a granulator; and
   D. drying granules from the granulator.

5. The granules of amino acid composition of claim 1, wherein the composition has a water-dissolved clearness time of less than 10 minutes.

6. The granules of amino acid composition of claim 1, wherein the composition has a water solution turbidity of less than 30 NTU.

7. The granules of amino acid composition of claim 1, wherein the one or more amino acids are in free form.

* * * * *